US00PP19084P2

(12) United States Plant Patent
Miyano

(10) Patent No.: US PP19,084 P2
(45) Date of Patent: Aug. 12, 2008

(54) ***ANTIRRHINUM* PLANT NAMED 'KEIANANZUREM'**

(50) Latin Name: *Antirrhinum hybrida*
Varietal Denomination: Keianzurem

(75) Inventor: Shinya Miyano, Tounosyou-machi (JP)

(73) Assignee: Keisei Rose Nurseries, Tokyo (JP)

( * ) Notice: Subject to any disclaimer, the term of this patent is extended or adjusted under 35 U.S.C. 154(b) by 0 days.

(21) Appl. No.: 11/799,079

(22) Filed: Apr. 30, 2007

(51) Int. Cl.
*A01H 5/00* (2006.01)

(52) U.S. Cl. ..... Plt./322
(58) Field of Classification Search ..... Plt./322
See application file for complete search history.

*Primary Examiner*—Annette H Para
(74) *Attorney, Agent, or Firm*—C. A. Whealy

(57) ABSTRACT

A new and distinct cultivar of *Antirrhinum* plant named 'Keiananzurem', characterized by its vigorous, upright and mounded plant habit; freely branching habit and short internodes; dense and bushy plant form; numerous soft orange and yellow bi-colored flowers; long flowering period; and good garden performance.

1 Drawing Sheet

Botanical designation: *Antirrhinum hybrida.*
Cultivar denomination: 'Keiananzurem'.

BACKGROUND OF THE INVENTION

The present invention relates to a new and distinct cultivar of *Antirrhinum,* botanically known as *Antirrhinum hybrida* and hereinafter referred to by the name 'Keiananzurem'.

The new *Antirrhinum* is a product of a planned breeding program conducted by the Inventor in Chiba, Japan. The objective of the breeding program is to create new compact and freely flowering potted *Antirrhinums* with unique flower coloration.

The new *Antirrhinum* originated from across-pollination in Chiba, Japan in June, 2000 of two unidentified proprietary selections of *Antirrhinum hybrida,* not patented. The cultivar Keiananzurem was discovered and selected by the Inventors as a flowering plant from within the progeny of the stated cross-pollination in a controlled environment in Chiba, Japan.

Asexual reproduction of the new *Antirrhinum* by cuttings in a controlled environmental in Chiba, Japan since May, 2001, has shown that the unique features of this new *Antirrhinum* are stable and reproduced true to type in successive generations.

SUMMARY OF THE INVENTION

The cultivar Keiananzurem has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Keiananzurem'. These characteristics in combination distinguish 'Keiananzurem' as a new and distinct cultivar of *Antirrhinum:*

1. Vigorous, upright and mounded plant habit.
2. Freely branching habit and short internodes; dense and bushy plant form.

3. Numerous soft orange and yellow bi-colored flowers.
4. Long flowering period.
5. Good garden performance.

Plants of the new *Antirrhinum* differ from plants of the female parent selection primarily in flower color as plants of the female parent selection have white and red purple bi-colored flowers.

Plants of the new *Antirrhinum* differ from plants of the male parent selection primarily in plant size as plants of the new *Antirrhinum* are taller than plants of the male parent selection.

Plants of the new *Antirrhinum* can be compared to plants of the cultivar Sultan Yellow, not patented. In side-by-side comparisons, plants of the new *Antirrhinum* and the cultivar Sultan Yellow differed in the following characteristics:

1. Plants of the new *Antirrhinum* were more mounding than and not as creeping as plants of the cultivar Sultan Yellow.
2. Plants of the new *Antirrhinum* were taller and broader than plants of the cultivar Sultan Yellow.
3. Plants of the new *Antirrhinum* had larger leaves than plants of the cultivar Sultan Yellow.
4. Plants of the new *Antirrhinum* had larger flowers than plants of the cultivar Sultan Yellow.
5. Plants of the new *Antirrhinum* had the cultivar Sultan Yellow differed in flower color.

BRIEF DESCRIPTION OF THE PHOTOGRAPHS

The accompanying colored photographs illustrate the overall appearance of the new *Antirrhinum,* showing the colors as true as it is reasonably possible to obtain in colored reproductions of this type. Colors in the photographs may differ slightly from the color values cited in the detailed botanical description which accurately describe the colors of the new *Antirrhinum.*

The photograph at the top of the sheet comprises a side perspective view of a typical flowering plant of 'Keiananzurem' grown in a container.

The photograph at the bottom of the sheet is a close-up view of typical flowers of 'Keiananzurem'.

DETAILED BOTANICAL DESCRIPTION

The aforementioned photographs and following observations, measurements and values describe plants grown in Chiba, Japan, under commercial practice during the spring in an outdoor nursery with day temperatures ranging from about 2° C. to about 20° C. and night temperatures ranging from about −4° C. to about 7° C. Plants had been growing for about ten months in 21-cm containers when the photographs and description were taken. In the following description, color references are made to The Royal Horticultural Society Colour Chart, 2001 Edition, except where general terms of ordinary dictionary significance are used.

Botanical classification: *Antirrhinum hybrida* cultivar Keiananzurem.

Parentage:

*Female, or seed, parent.*—Unidentified proprietary selection of *Antirrhinum hybrida,* not patented.

*Male, or pollen, parent.*—Unidentified proprietary selection of *Antirrhinum hybrida,* not patented.

Propagation:

*Type.*—By vegetative cuttings.

*Time to initiate roots.*—About 10 days at 20° C. to 25° C.

*Time to produce a rooted young plant.*—About 25 days at 20° C. to 25° C.

*Root description.*—Fine, fibrous and fleshy, white in color.

*Rooting habit.*—Freely branching; dense.

Plant description:

*Plant form/habit.*—Vigorous, upright and mounded plant habit; broad inverted triangle. Freely branching habit with short internodes; dense and bushy plant form.

*Plant height.*—About 35 cm.

*Plant width* (*spread*).—About 60 cm.

*Lateral branches.*—Length: About 25 cm. Diameter: About 2 mm. Internode length: About 1.5 mm. Strength: Moderately strong. Texture: Pubescent. Color: 143C.

Foliage description:

*Arrangement.*—Alternate, simple; sessile.

*Length.*—About 4.2 cm.

*Width.*—About 1.1 cm.

*Shape.*—Elliptic.

*Apex.*—Obtuse.

*Base.*—Obtuse.

*Margin.*—Entire.

*Texture, upper and lower surfaces.*—Pubescent.

*Venation pattern.*—Pinnate; reticulate.

*Color.*—Developing and fully expanded leaves, upper surface: 139A; venation, 139A. Developing and fully expanded leaves, lower surface: 137B; venation, 137B.

Flower description:

*Flower type/habit.*—Single bi-labiate flowers arranged in terminal racemes; flowers face outward. Freely flowering habit with about four flowers per inflorescence and numerous flowers developing per plant.

*Fragrance.*—Sweet.

*Natural flowering season.*—Continuous flowering throughout the spring in Japan. Flowers not persistent.

*Postproduction longevity.*—Flowers last about five days on the plant.

*Flower buds.*—Height: About 2.1 cm. Diameter: About 1 cm. Shape: Oval. Color: 31C.

*Flower diameter.*—About 2.5 cm.

*Flower depth* (*height*).—About 3 cm.

*Petals.*—Quantity per flower: Upper lip, two-lobed; lower lip, three-lobed; petals fused at the base. Length: About 3.2 cm. Width: About 2.4 cm. Shape: Upper, roughly cordate; lower, roughly obovate. Apex: Rounded. Margin: Entire; weakly undulate. Texture, upper and lower surfaces: Smooth, glabrous; satiny. Color: Upper petal, when opening and fully opened, upper surface: 28C. Lower petal, when opening and fully opened, upper surface: 28C; towards the base, 6A. Upper and lower petals, when opening and fully opened, lower surface: 28C.

*Sepals.*—Quantity per flower; Typically five in a single whorl. Length: About 2.1 cm. Width: About 1 mm. Shape: Narrowly oblong. Apex: Rounded. Margin: Entire. Texture, upper and lower surfaces: Smooth, glabrous; satiny. Color, upper and lower surfaces: 141C.

*Pedicels.*—Length: About 7.2 mm. Diameter: About 1 mm. Strength: Strong. Texture: Smooth, glabrous. Color: 141C.

*Reproductive organs.*—Stamens: Quantity per flower: Typically five. Anther size: About 2 mm by 1 mm. Anther shape: Ellipse-like. Anther color: 12A. Filament color: 155D. Pollen amount: Moderate. Pollen color: 12A. Pistils: Quantity per flower: One. Pistil length: About 1.2 cm. Stigma shape: Oval. Stigma color: 196A. Style length: About 2 cm. Style color: 64B. Ovary color: 66D.

*Seed.*—Shape: Spherical. Length: About 0.8 mm. Diameter: About 0.8 mm. Color: 200B.

Disease/pest resistance: Plants of the new *Antirrhinum* have not been noted to be resistant to pathogens and pests common to *Antirrhinum.*

Garden performance: Plants of the new *Antirrhinum* have been observed to have excellent garden performance and tolerate rain, wind and temperatures ranging from about −3° C. to about 25° C.

It is claimed:

1. A new and distinct *Antirrhinum* plant named 'Keiananzurem' as illustrated and described.

* * * * *

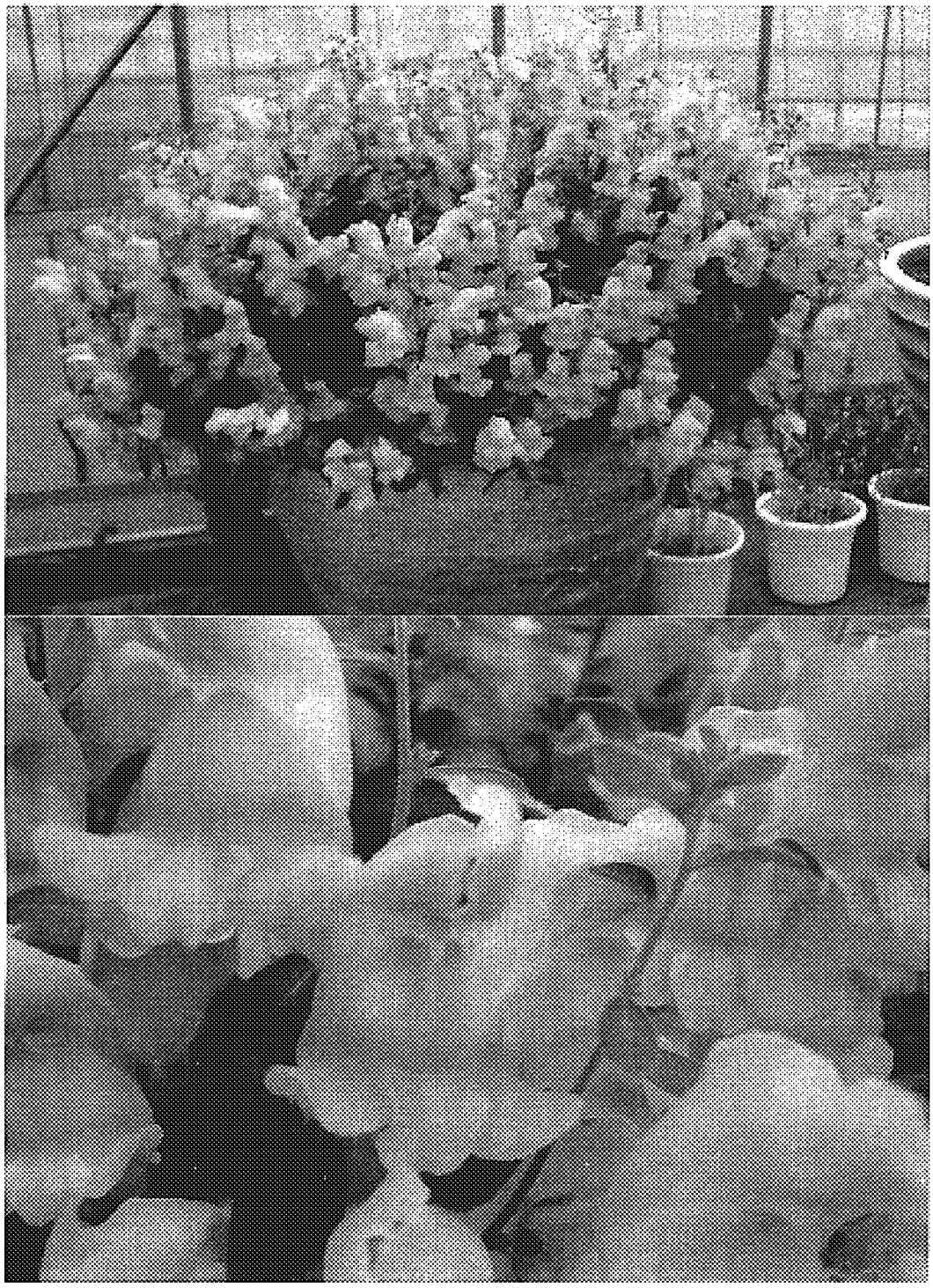

UNITED STATES PATENT AND TRADEMARK OFFICE

CERTIFICATE OF CORRECTION

PATENT NO. : PP 19,084 P2
APPLICATION NO. : 11/799079
DATED : August 12, 2008
INVENTOR(S) : Shinya Miyano It is certified that error appears in the above-identified patent and that said Letters Patent is hereby corrected as shown below:

Title page, item 50 should read
--Varietal Denomination: Keiananzurem--

Signed and Sealed this

Twenty-seventh Day of January, 2009

JOHN DOLL
*Acting Director of the United States Patent and Trademark Office*